(12) United States Patent
Shikata et al.

(10) Patent No.: US 8,075,487 B2
(45) Date of Patent: Dec. 13, 2011

(54) ULTRASOUND DIAGNOSIS SYSTEM INCLUDING A MOTOR DRIVING MULTIPLANE ULTRASOUND PROBE AND IMAGE DATA ACQUIRING METHOD

(75) Inventors: Hiroyuki Shikata, Tochigi-ken (JP);
Hideki Kosaku, Tochigi-ken (JP);
Takashi Takeuchi, Tochigi-ken (JP)

(73) Assignees: Kabushiki Kaisha Toshiba, Tokyo (JP);
Toshiba Medical Systems Corporation, Otawara-sho (JP)

( * ) Notice: Subject to any disclaimer, the term of this patent is extended or adjusted under 35 U.S.C. 154(b) by 912 days.

(21) Appl. No.: 12/098,141

(22) Filed: Apr. 4, 2008

(65) Prior Publication Data

US 2008/0249418 A1    Oct. 9, 2008

(30) Foreign Application Priority Data

Apr. 5, 2007    (JP) .................... 2007-099245

(51) Int. Cl.
*A61B 8/00* (2006.01)
*A61B 8/14* (2006.01)
(52) U.S. Cl. .................. 600/445; 600/444; 600/459
(58) Field of Classification Search .................. None
See application file for complete search history.

(56) References Cited

U.S. PATENT DOCUMENTS

| | | | | |
|---|---|---|---|---|
| 5,402,793 A | * | 4/1995 | Gruner et al. | 600/447 |
| 5,479,930 A | * | 1/1996 | Gruner et al. | 600/459 |
| 5,575,288 A | * | 11/1996 | Sliwa et al. | 600/445 |
| 5,630,417 A | * | 5/1997 | Petersen et al. | 600/443 |
| 5,634,466 A | * | 6/1997 | Gruner | 600/459 |
| 5,720,285 A | * | 2/1998 | Petersen | 600/459 |
| 6,110,121 A | * | 8/2000 | Lenker | 600/463 |
| 6,471,653 B1 | * | 10/2002 | Jordfald et al. | 600/462 |
| 6,547,739 B2 | * | 4/2003 | Jordfald et al. | 600/462 |
| 2002/0095088 A1 | * | 7/2002 | Jordfald et al. | 600/462 |
| 2003/0229286 A1 | * | 12/2003 | Lenker | 600/462 |
| 2004/0210141 A1 | * | 10/2004 | Miller | 600/459 |
| 2008/0009745 A1 | * | 1/2008 | Hossack et al. | 600/463 |
| 2008/0146918 A1 | * | 6/2008 | Magnin et al. | 600/437 |
| 2008/0183080 A1 | * | 7/2008 | Abraham | 600/466 |
| 2009/0036780 A1 | * | 2/2009 | Abraham | 600/459 |
| 2009/0105597 A1 | * | 4/2009 | Abraham | 600/466 |

FOREIGN PATENT DOCUMENTS

JP    2006-312103    11/2006

* cited by examiner

*Primary Examiner* — Long V. Le
*Assistant Examiner* — Angela M Hoffa
(74) *Attorney, Agent, or Firm* — Oblon, Spivak, McClelland, Maier & Neustadt, L.L.P.

(57) ABSTRACT

An ultrasound diagnosis system including a motor driving multi-plane ultrasound probe for acquiring image data at a voluntary scanning plane in a body of a patient is provided. The data acquisition is performed by driving rotation of a plurality of transducers arranged in a head portion of the probe toward a target angle of a prescribed rotation range by driving an arranged surface of the plurality transducers so as to make a plurality of scanning planes toward a first direction in a normal mode. The driving direction of the head portion is automatically reversed by 180 degrees to a second direction opposite to the first direction at a high speed in a reverse mode when the rotation angle of the head portion arrives at the target angle. The reversed head portion can continue to acquire image data at the same scanning planes to the previous scanning planes of the rotation drive to the first direction.

15 Claims, 13 Drawing Sheets

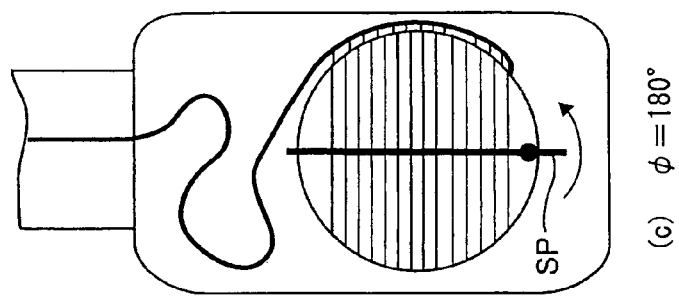
FIG. 5A
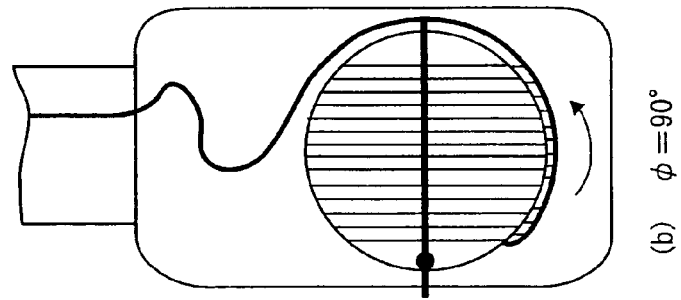
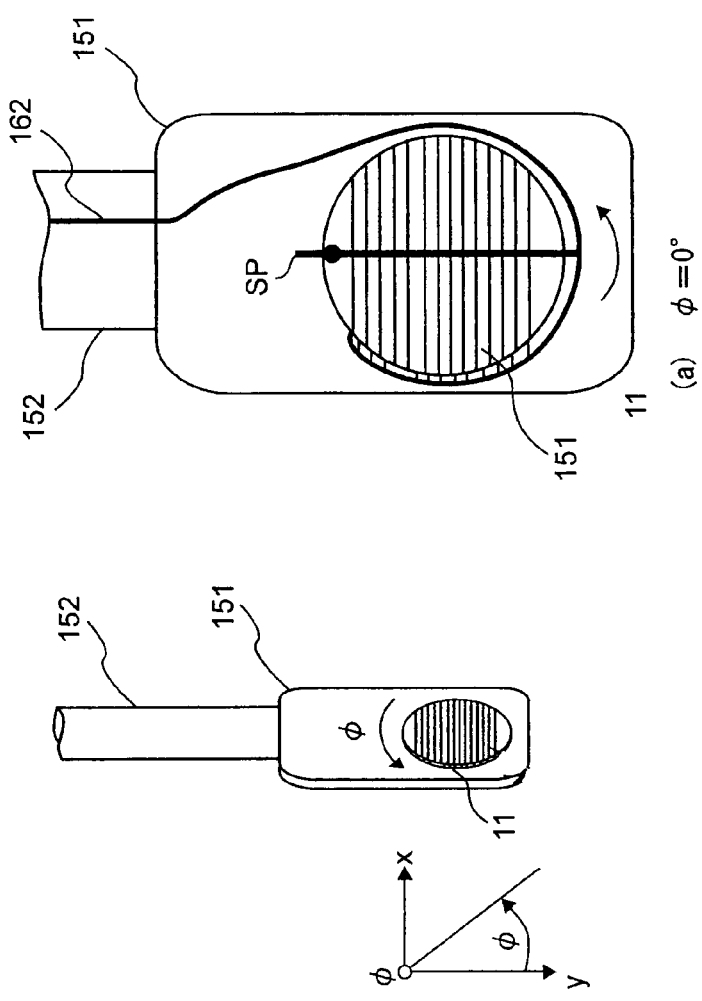
FIG. 5B

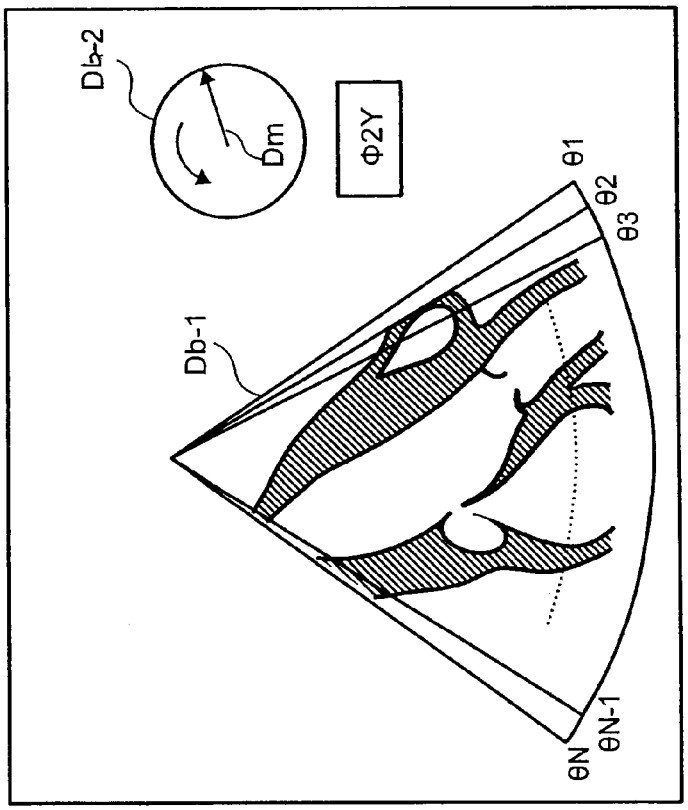
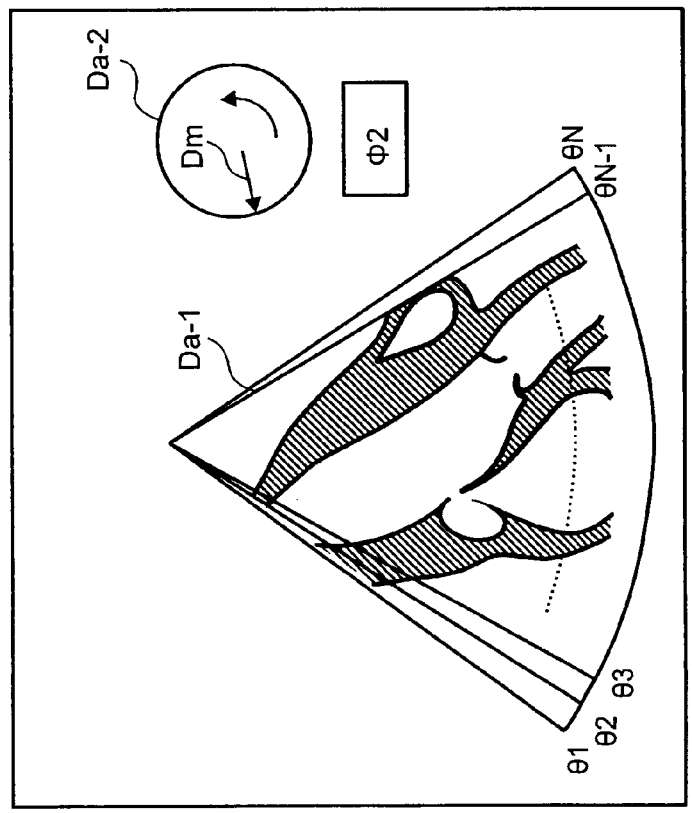
FIG. 11A
FIG. 11B

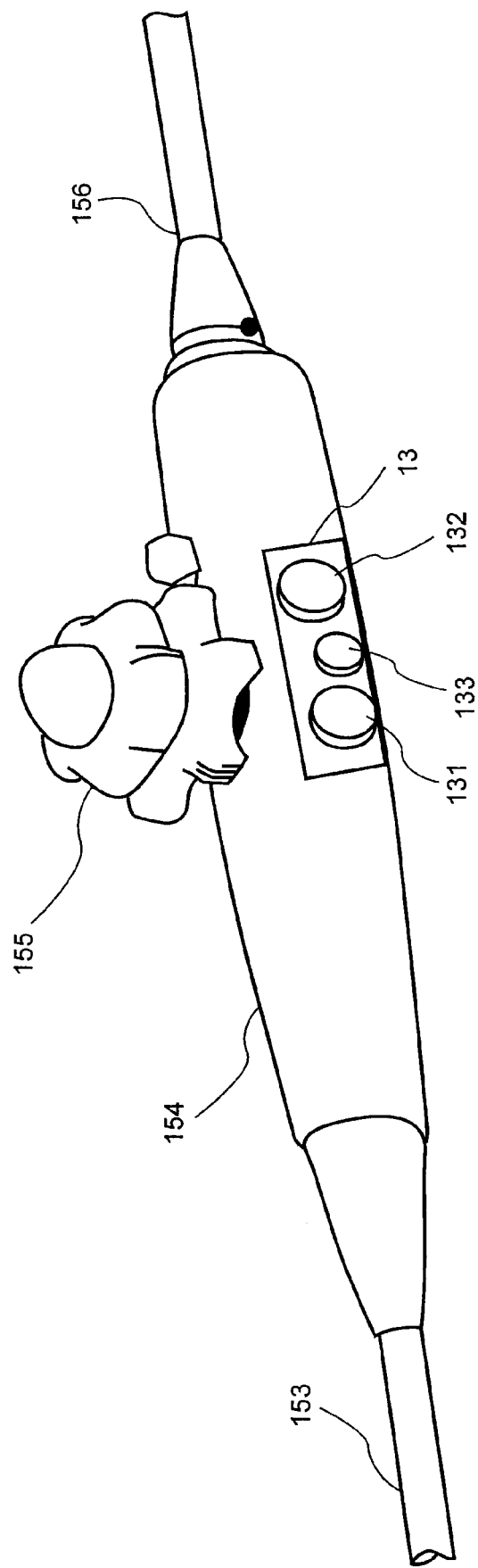

ULTRASOUND DIAGNOSIS SYSTEM INCLUDING A MOTOR DRIVING MULTIPLANE ULTRASOUND PROBE AND IMAGE DATA ACQUIRING METHOD

CROSS-REFERENCE TO RELATED APPLICATIONS

This application claims priority to, and the benefit of, Japanese Patent Application No. 2007-99245, filed on Apr. 5, 2007, the contents of which are expressly incorporated herein by reference, in their entirety.

BACKGROUND OF THE INVENTION

A. Field of the Invention

The present invention relates to an ultrasound diagnosis system including an ultrasound probe, and more particularly, to an ultrasound diagnosis system including a motor driving multi-plane type ultrasound probe that can acquire image data at a plurality of scanning planes, by rotating an arranged surface of ultrasound transducers in a head portion of the probe across a prescribed range of angles.

B. Background of the Invention

An ultrasound diagnosis system transmits ultrasound from ultrasound transducers (hereinafter: "transducers) installed in a head portion of the ultrasound probe to an object, such as a patient. The transducers receive ultrasounds reflected from the object as image data that is generated in accordance with differences of acoustic impedances of an organ of the object. The received image data is processed as an image of the organ and displayed on a monitor.

Since the ultrasound diagnosis system can easily obtain and observe two dimensional images in real-time by simply touching an ultrasound probe on a patient's body, it is widely used in various diagnoses. To examine a function or the status of an organ in a patient's body, an ultrasound diagnosis system acquires vital data based on reflected ultrasounds from an organ or blood cells of the object. To perform the ultrasound diagnosis, two types of images (B mode images and color Doppler images) are used. B mode images are acquired by using a method of ultrasound reflections. Color Doppler images are acquired by using an ultrasound Doppler method.

In particular, a trans-esophageal ultrasound diagnosis is used for performing a cardiac diagnosis. To perform the trans-esophageal ultrasound diagnosis, head portion installed ultrasound transducers are inserted into the esophagus of a patient body so as to place the transducers at an appropriate position in a vicinity to a heart while avoiding the influences of ribs and a lung, since these organs are usually prevent ultrasound transmission and reception to and from the heart. By placing the transducers in the vicinity of a heart, the trans-esophageal ultrasound diagnosis can obtain and observe a high resolution image data of the heart or a vicinity blood tube system.

Typically, the trans-esophageal ultrasound diagnosis uses an ultrasound probe including a head portion in which a plurality of transducers are arranged in a surface. In order to insert the probe into a patient body, the head portion is connected to a flexible guiding tube that is constructed similar to an endoscope. The arranged surface of the plurality of transducers is rotated on a vertical axis to the surface in order to acquire image data at a desired angle. The arranged ultrasound emission surface is hereinafter referred to as a "scanning plane." In the trans-esophageal ultrasound diagnosis, it is conventionally difficult to place the scanning plane at a desired direction by using an angle knob as used in an endoscope, since the surface is needed to move in a limited narrow area of an esophagus. Accordingly, it has been proposed to use a motor driving multi-plane type ultrasound probe for the trans-esophageal ultrasound diagnosis. The motor driving multi-plane type ultrasound probe can place the scanning planes at desired directions by a motor driven rotation of the transducers.

In particular, since the motor driving multi-plane type ultrasound probe has good operability, it is useful as a cardiac diagnosis to easily and accurately obtain cardiac image data by rotating the transducers installed in a head portion of an ultrasound probe. Conventionally, two types of the motor driving multi-plane type ultrasound probe have been proposed. One is a successive rotation type probe in which the transducers are successively rotated in a prescribed direction. The other is a reverse rotation type probe in which an arranged surface of the transducers is rotated in one direction in a prescribed angle range from a zero degree angle to a target angle of less than 180 degrees. In the reverse rotation type probe, when the transducers are rotated up to the target angle, an operator moves the transducers in an opposite (reversing) direction as suggested in Japanese Patent Application Publication 2006-312103.

In the successive rotation type motor drive multi-plane ultrasound probe, the transducers in the head portion of the probe transmit signals through a slip ring provided between a rotation portion of the head and a fixed portion of the head. The successive rotation type probe has various problems and defects. Due to the size of the slip ring installed in the head portion, an external size of the head portion of the successive rotation type motor drive multi-plane ultrasound probe becomes a larger size. Consequently, it becomes difficult to insert the head portion into an esophagus of a patient without causing the patient to experience pain. Further, the slipping noises generated from the slip ring cause deteriorations in the quality of the generated image data to occur.

In the reverse rotation type motor drive multi-plane ultrasound probe, a plurality of the transducers installed in a head portion of the probe is connected to each of the signal lines printed on a flexible printed circuit board (FPC) with a narrow pitch between each of the signal lines. Consequently, it becomes possible to make the head portion of the probe in a smaller size than the head for the successive rotation type probe. Since the FPC connection in the head of the reverse rotation type ultrasound probe does not generate such slipping noises as in the successive rotation type ultrasound probe, it becomes possible to acquire better quality image data.

Usually, the reverse rotation type motor driving multi-plane ultrasound probe includes two instruction buttons for respectively instructing rotation in a first direction, for instance, a clockwise (CW) direction and a second direction opposite to the first direction, i.e., a counterclockwise (CCW) direction. The transducers installed in a head portion are rotated in a desired direction by selecting the direction instruction buttons provided in an angle portion of the probe. For instance, suppose that a CCW rotation direction is selected by using a CCW button, image data is collected at a plurality of scanning planes by successively rotating the transducers in a CCW direction in a predetermined angle range within 180 degrees.

In conventional techniques, when the transducers approach a target angle of, for instance, almost 180 degrees by rotating in an instructed CCW direction, there exists a need for an operator to select a reverse CW direction by using the CW instruction button in order to reverse the transducers 180 degrees so as to place the scanning plane at an adjoin angle position to the target angle in the CCW direction. Thus, when the transducers approach the vicinity of the target angle, there exists a need for an operator to change the rotation speed of the transducers from a normal speed to a lower speed in order to achieve an accurate head angle position. These operations are complicated and burdensome for an operator. Thus, it takes a lot of time for setting the transducers in a desired angle position. Since it largely reduces efficiencies of observations through ultrasound images, the conventional reverse rotation type motor driving multi-plane ultrasound probe also has serious problems.

SUMMARY OF THE INVENTION

To solve the above-mentioned conventional problems and defects, the present invention provides a new ultrasound diagnosis system including a reverse rotation motor driving multi-plane ultrasound probe and a scanning method. The ultrasound diagnosis system including a motor drive multi-plane type ultrasound probe consistent with the present invention can automatically rotate the transducers in a first direction to acquire image data in a prescribed target angle and the transducers are automatically rotated in a reverse direction at a high speed so as to acquire image data secretive to the image data acquired at the target angle by rotating the transducers in the first direction. The scanning method consistent with the present invention can automatically place successive scanning planes over a target angle in a designated rotation direction. When the motor driven transducers reach a target angle in a first direction for acquiring image data, the transducers are automatically reversed to operate in a second direction by reserving the transducers at a high speed with ceasing acquisition of image data. After completing the reversion, the transducers are again rotated in the first direction to acquire image data at successive rotation angles.

According to an ultrasound diagnosis system including a motor driving multi-plane type ultrasound probe for use with the present invention, because the transducers are automatically rotated in a reverse direction at a higher speed when a rotated angle of the transducers exceeds a target angle, a user or operator can freely place the scanning planes not withstanding a limited angle range of rotation. Thus, it becomes possible to set a scanning plane in a short time. Further, according to the present invention, it become possible to make a tip portion of a motor driving multi-plane type ultrasound probe in a small size by coupling to the ultrasound diagnosis system through a flexible probe cable in order to control the scanning planes of the transducers. Consequently, it can reduce pain to a patient. An ultrasound probe consistent with the present invention can set a target rotation range of a plurality of transducers from an angle of zero degrees to an angle over 180 degrees. This can restrict frequent occurrences of reversing operations to as few as possible. This is beneficial to reduce displayed image due to frequent freezes of displayed images as a result of frequent reverse operations. Further, according to the present invention, it can reduce the load to a rotation drive mechanism for the transducers.

One aspect of the ultrasound diagnosis system consistent with the present invention is an ultrasound diagnosis system including a motor driving multi-plane type ultrasound probe for acquiring image data at a voluntary scanning plane by rotating a plurality of transducers arranged in a head portion to a prescribed target angle range; the ultrasound diagnosis system comprising:

a rotation drive instructing unit configured to instruct rotation drive of the head portion;

a rotation angle detecting unit configured to detect a rotation angle of the head portion;

a rotation mechanism driving unit configured to drive rotation of the head portion; and a rotation mechanism controlling unit configured to control the rotation mechanism driving unit based on both a rotation drive instruction signal supplied from the rotation drive instructing unit and a rotation angle detection signal supplied from the rotation angle detecting unit;

wherein the rotation mechanism controlling unit controls a rotation drive of the plurality of transducers in a normal rotation drive mode for acquiring image data in the prescribed target angle range toward a first direction and reverses the plurality of transducers in a reverse rotation drive mode in a second direction opposite to the first direction, up to a prescribed reversing angle when the rotation of the head portion exceeds the target range of the rotation angle;

the rotation mechanism controlling unit further controls a rotation drive of the reversed head portion under the normal rotation drive mode to the first direction when the rotation drive instruction signal is further supplied.

One aspect of the scanning method for an ultrasound diagnosis system consistent with the present invention is a scanning method for an ultrasound diagnosis system including a motor drive multi-plane type ultrasound probe for acquiring image data at a voluntary scanning plane angle by rotating a plurality of transducers arranged in a head portion toward a target range of rotation angle, the scanning method for the ultrasound diagnosis system comprising:

setting rotation drive parameters of the head portion;

inputting a rotation drive instruction signal for the head portion;

detecting a detection signal of a present rotation angle of the head portion; and controlling a drive of a rotation drive mechanism of the head portion based on both the rotation drive instruction signal for the head portion and the detection signal of the rotation angle;

wherein the rotation drive mechanism performs a control of a rotation drive of the head portion under a normal rotation drive mode for acquiring image data in the target range of rotation angle toward a first direction and reverses the head portion under a reverse rotation drive mode in a second direction opposite to the first direction by a prescribed angle when the rotation of the head portion exceeds the target range of rotation angle in the first direction;

the rotation drive mechanism further performs a control of a rotation drive of the reversed head portion under the normal rotation drive mode to the first direction when the rotation drive instruction signal is still supplied.

According to the ultrasound diagnosis system including a motor drive multi-plane type ultrasound probe and the scanning method, consistent with the present invention, a plurality of transducers one dimensionally arranged in a head portion of the ultrasound probe, acquires image data at a plurality of scanning planes by rotating the transducers along a first direction to a target rotation angle in a prescribed range. When image data acquisition is executed over the target rotation angle, it becomes possible to continue at the successive scanning planes to the plurality of scanning planes in the first direction by automatically reversing the arranged surface of the transducers at a high speed in a second direction opposite to the first direction.

BRIEF DESCRIPTION OF THE DRAWINGS

The accompanying drawings, which are incorporated in and constitute part of this specification, illustrate various embodiments and/or features of the present invention.

FIGS. 5A and 5B illustrate the relationship between a rotation drive direction of the transducers arranged in a head portion of the motor drive multi-plane type ultrasound probe as shown in FIG. 4; rotation drive directions of scanning planes, and installing conditions of a signal cable connected to each of the transducers.

FIGS. 11A and 11B show examples of monitor displays of the image data acquired in the normal rotation drive mode of the head portion and image data acquired just after performing a head rotation in reverse rotation mode, as explained in FIG. 10.

FIG. 12 illustrates another embodiment of the knob handling portion of the ultrasound probe.

DESCRIPTION OF THE EMBODIMENTS

Figure 1:
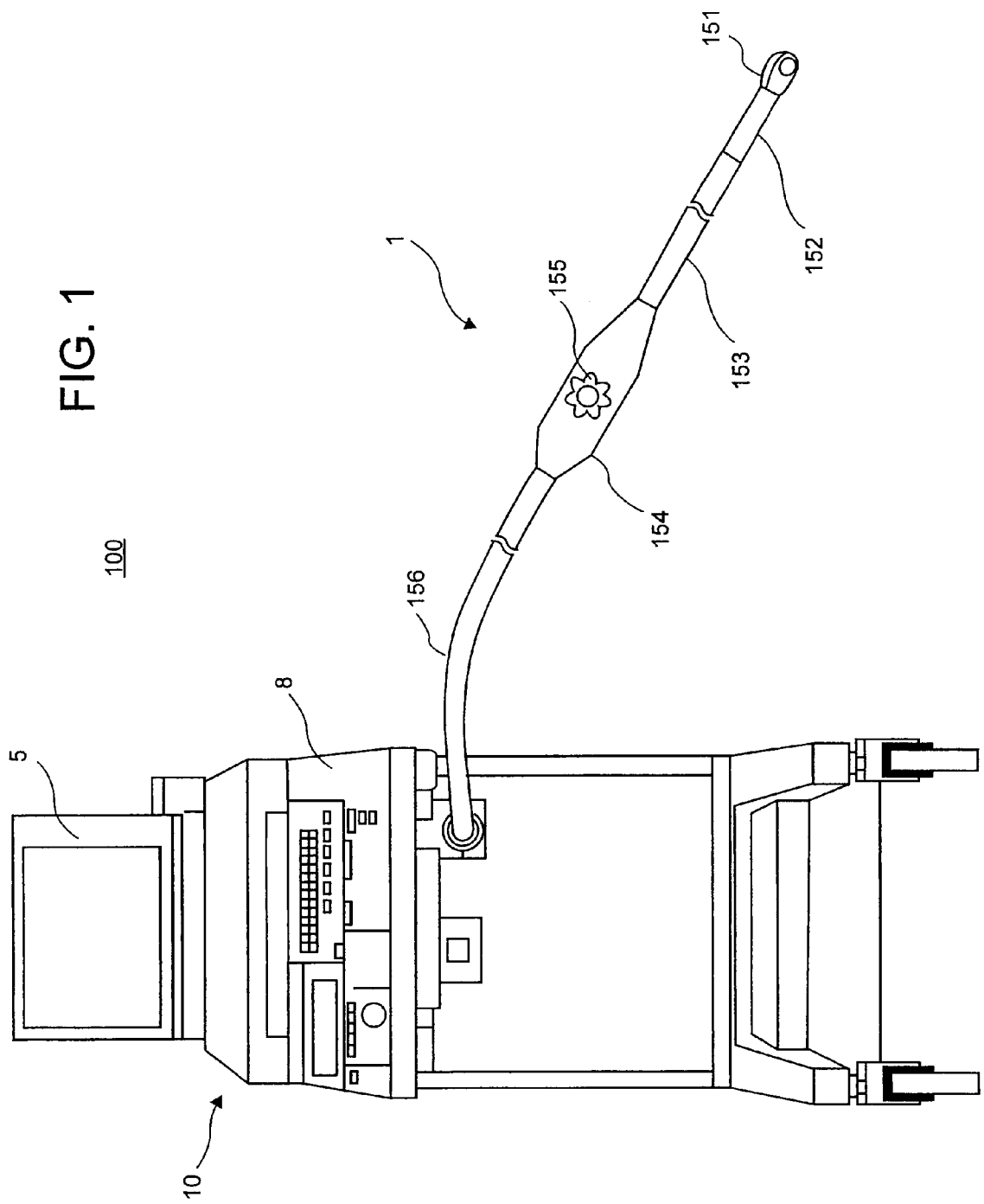
FIG. 1 is an external view of an embodiment of a ultrasound diagnosis system including a motor drive multi-plane type ultrasound probe according to the present invention.

As shown in FIG. 1, an ultrasound diagnosis system 100 consistent with the present invention is comprised of a diagnosis main body 10 and a motor drive multi-plane ultrasound probe 1 coupled to the diagnosis main body 10 in order to transmit and receive ultrasound to and from a diagnosis object portion of a patient. The motor drive multi-plane ultrasound probe 1 is electrically connected to the main body 10 through a tip portion 151 for insertion into a patient body, for example an esophagus of the patient, an angle portion 152, a flexible trans-guiding portion 153 and a knob handling portion 154 that is connected to the trans-guiding portion 153. The tip portion 151 and the angle portion 152 are inserted into a target position in a patient's body through the trans-guiding portion 153.

Figure 2:
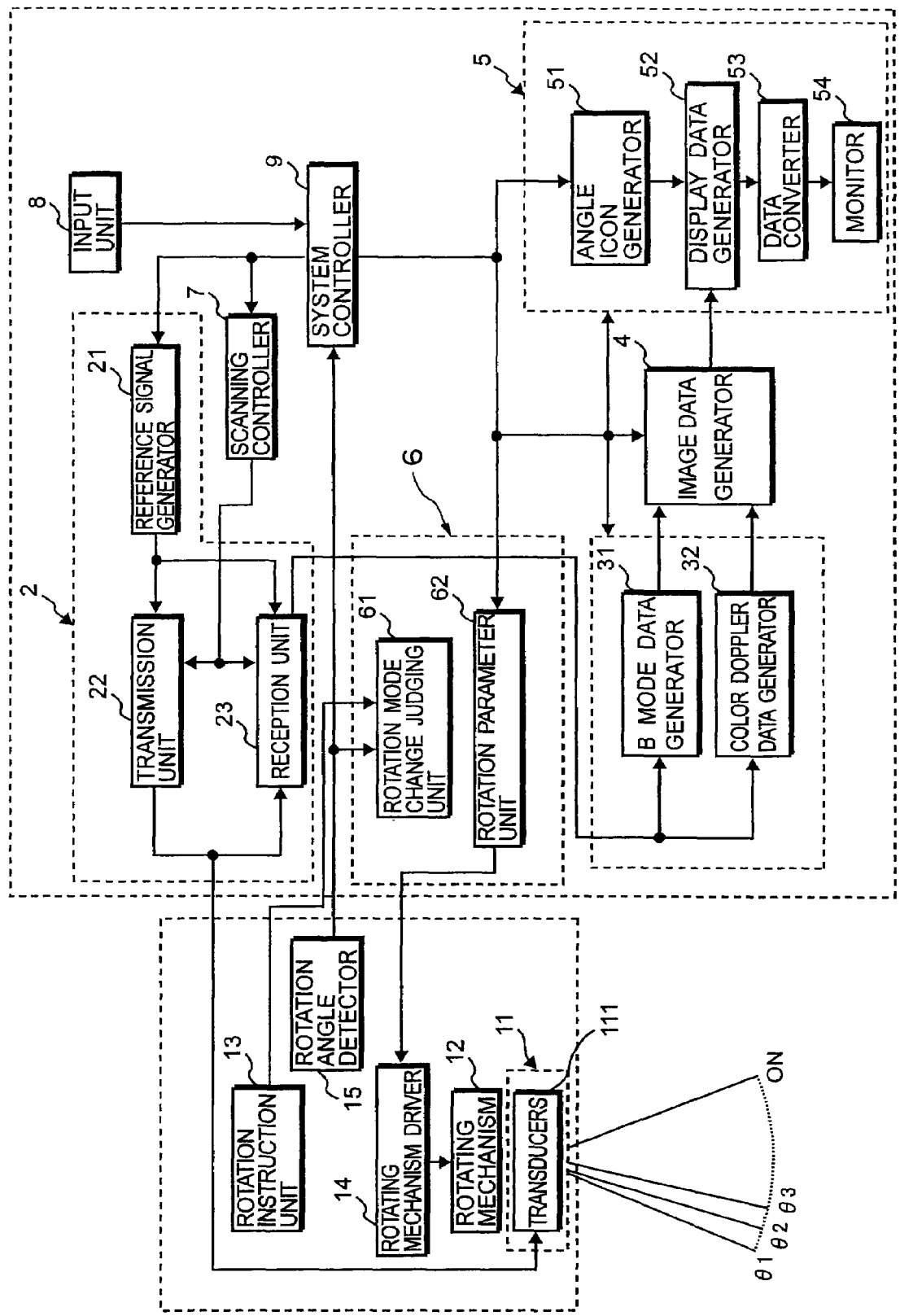
FIG. 2 is a block diagram illustrating a construction of the ultrasound diagnosis system including a motor drive multi-plane type ultrasound probe, as shown in FIG. 1.
Figure 3:
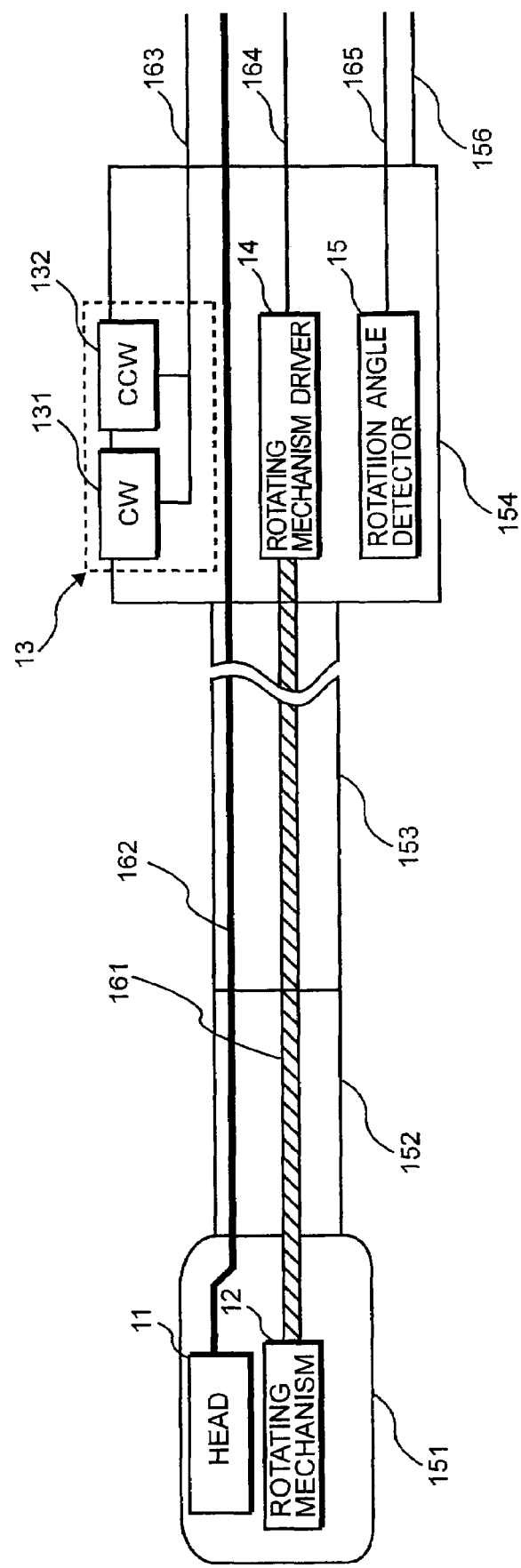
FIG. 3 is a block diagram illustrating a construction of the motor drive multi-plane type ultrasound probe as shown in FIG. 1.
Figure 4:
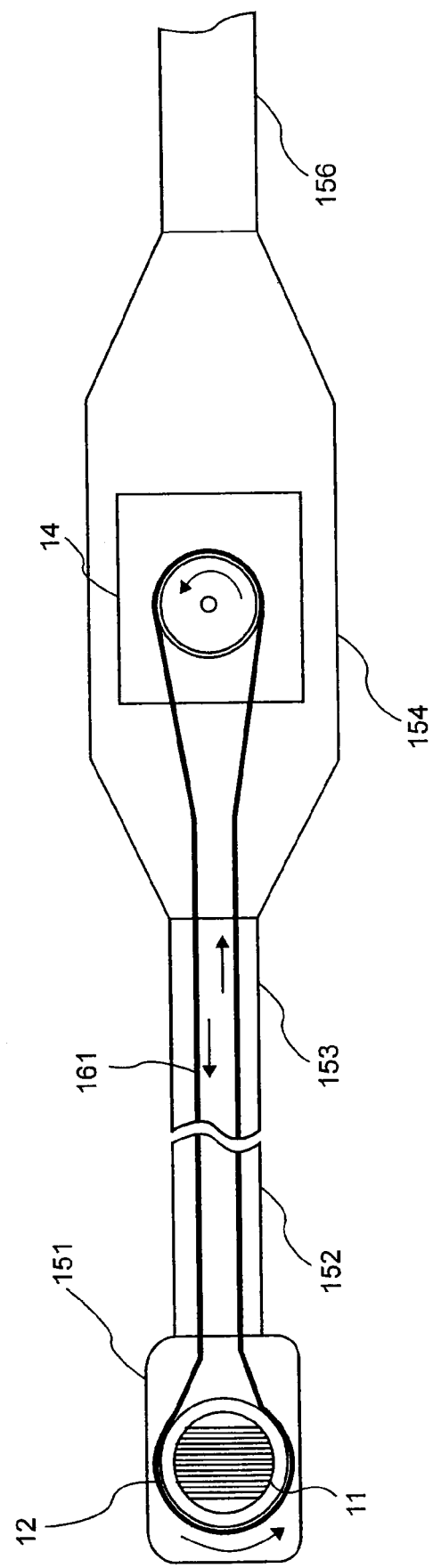
FIG. 4 illustrates a method for transmitting driving power in the motor drive multi-plane type ultrasound probe shown in FIG. 3.

As shown in FIG. 3, the tip portion 151 of the ultrasound probe 1 includes a head portion 11 and a rotation drive mechanism 12. As shown in FIG. 4, the head portion 11 provides a plurality of, i.e., multi-channel transducers 111 (FIG. 2) arranged in one dimension. The plurality of transducers 111 is mounted so as to rotate around a center axis that is vertical to a surface of an arrangement of the plurality of transducers 111. Thus, a scanning plane constructed by the plurality of transducers 111 can rotate around the vertical axis. The multi-channel transducer in the head portion 11 is rotated in an instructed direction of rotation by the rotation drive mechanism 12 for acquiring image data. According to the present invention, the multi-channel transducer rotates, for instance, in a counterclockwise (first) direction in a normal rotation drive mode for acquiring image data, and rotates in a counterclockwise direction at a high speed in a reverse mode while ceasing acquisition of image data. As shown in FIG. 5A, an appropriate direction of scanning plane to a target position for a diagnosis is set by changing the vertical center axis to an arranged surface of the transducers.

Figure 6:
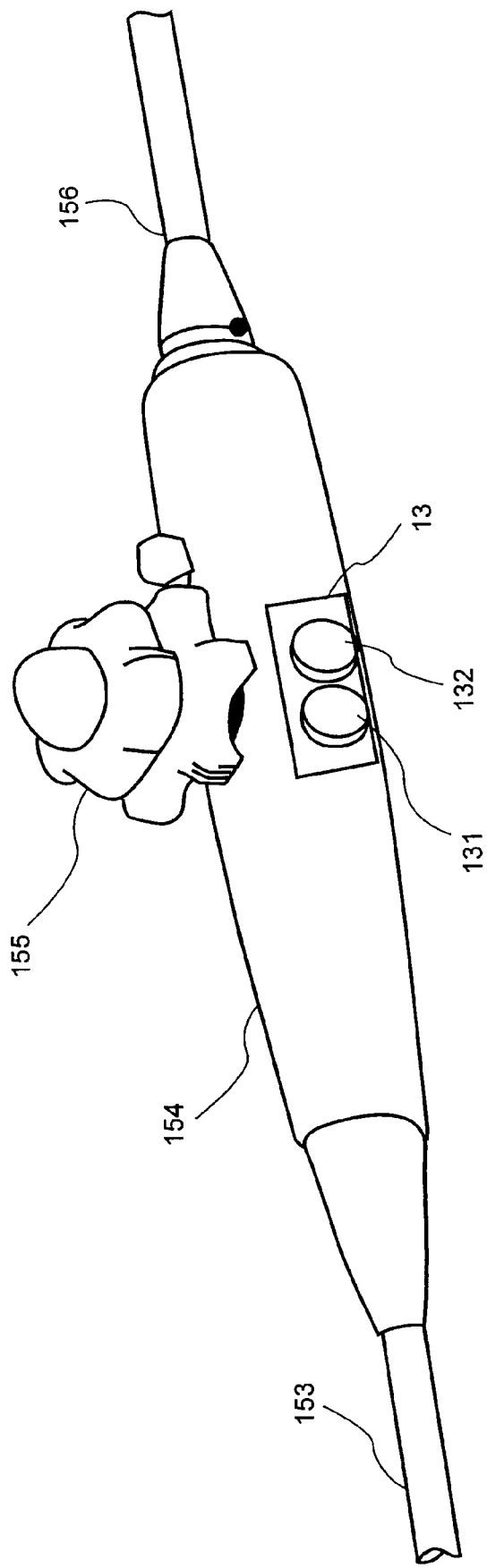
FIG. 6 is an external view of an embodiment of a knob handling portion of the motor drive multi-plane type ultrasound probe shown in FIG. 4.

As shown in FIGS. 1 and 6, the knob handling portion 154 of the ultrasound probe 1 provides an angle knob 155 for setting a center axis that is vertical to an arranging of the transducers to a desired direction by adjusting a curvature and a curving direction of the angle portion 152. As shown in FIG. 3, a rotation drive instructing unit 13, a rotating mechanism driver 14 and a rotation angle detecting unit 15 are provided in the knob handling portion 154. The rotation drive instructing unit 13 has two push buttons 131 and 132 in order to supply instruction signals of a rotation drive direction, a driving speed and a start of rotation drive to the head portion 11. One of the two push buttons instructs to rotate in a first direction and the other button instructs to rotate in a second direction. In the following embodiments, consistent with the present invention, a first direction is used for indicating a counter clockwise (CCW) direction and a second direction indicates a clockwise (CW) direction. The push button 132 supplies a rotation drive instructing signal for driving in the first direction. The push button 131 supplies a rotation drive instructing signal for driving in the second direction. Depending upon how these two buttons 131 and 132 are pushed, either a continuous rotation drive or a step rotation drive is instructed and a driving speed is set. For instance, a pushing strength or a pushing time of each of buttons selects either the continuous rotation drive or the step rotation drive and also sets the driving speed. As a practical matter, the stronger pressure and the longer time of pushing the button is pushed, the faster the driving speed is instructed. Further, when the button is pushed more than a prescribed time, step rotation drive in a normal mode changes to a continuous rotation drive.

The rotating mechanism driver 14 in the knob handling portion 154 supplies head rotation power to the head portion in the tip portion 151 through an angle wire 161. To transfer driving power, it is possible to use another transferring means, such as a flexible torque wire. The rotation angle detecting unit 15 in the knob handling portion 154 detects a present rotation angle of the head portion 11. For instance, the rotated angle data is detected by an encoder connected to a stepping motor used as the rotating mechanism driver 14 through a gear. A signal line 163 connected to the push buttons 131 and 132 in the rotation drive instructing unit 13 provided in the knob handling portion, a signal line 164 connected to the rotating mechanism driver 14 and a signal line 165 connected to the rotation angle detecting unit 15 are respectively coupled to a rotation mechanism controlling unit 6 in the diagnosis apparatus main body 10 through a flexible probe cable 156. The signal line 165 for the rotation angle detecting unit 15 is further connected to a system controller 9 in the diagnosis apparatus main body 10. A plurality of transducers in the head portion 11 is coupled to a transmission/reception unit 2 in the diagnosis apparatus main body 10 through a multi-channel signal cable 162 in the probe cable 156.

Again referring to FIG. 2, a construction of the diagnosis apparatus main body 10 for the ultrasound diagnosis system 100, in accordance with the present invention is described. As mentioned above, a plurality (M channels) of transducers 111 in the ultrasound probe is coupled to the transmission/reception unit 2 in the diagnosis apparatus main body 10 through a multi-channel (M) signal cable 162. The transmission/reception unit 2 includes a reference signal generator 21, a transmission unit 22 for supplying drive signals to a plurality of transducers 111 in the head based on the reference signal, and a reception unit 23 for adding received signals acquired from the plurality of transducers 111. The diagnosis apparatus main body 10 further includes an ultrasound data generator 3 for generating ultrasound data by processing the received signals from the reception unit 23 in the transmission/reception unit 2.

Figure 7:
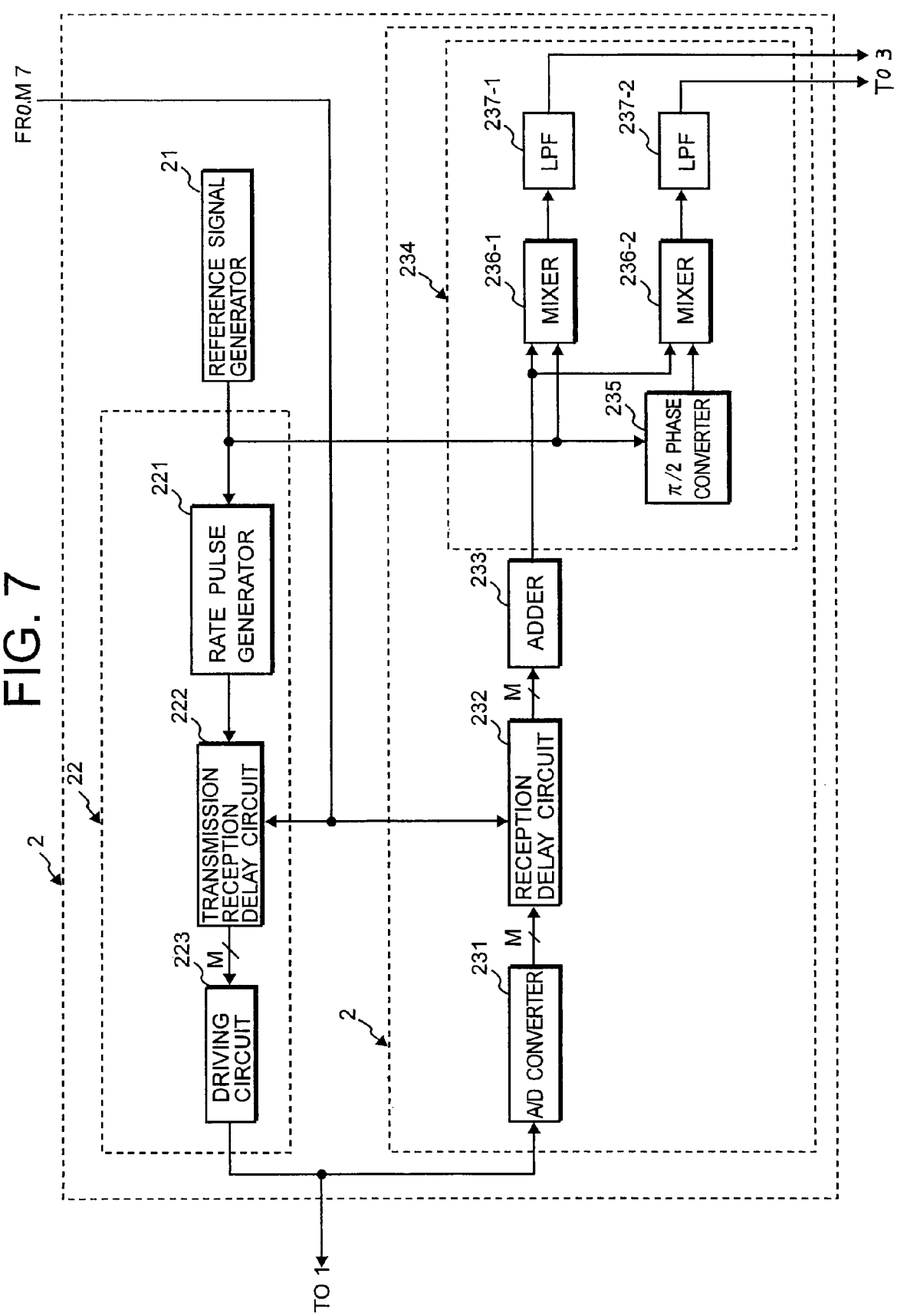
FIG. 7 is a block diagram illustrating a construction of an embodiment of a transmission/reception unit in the ultrasound diagnosis system shown in FIG. 2.

As depicted in FIG. 2, the reception unit 23 in the transmission/reception unit 2 includes (as shown in FIG. 7) an A/D converter 231, an M-channel reception delaying circuit 232, an adder 233 and an orthogonal detecting phase unit 234. The A/D converter 231 converts the M-channel receiving analog signals supplied from the transducers 111 to digital signals. The M-channel reception delaying circuit 232 gives a converging delaying time for converging an ultrasound wave reflected from at a prescribed depth and a deflecting delaying time for affording a strong reception directivity to an ultrasound wave received from a prescribed direction to the digital M-channel receiving signals converted in the A/D converter 231 based on a control signal supplied from the scanning controller 7 (FIG. 2). The adder 233 adds and composes M-channel receiving signals outputted from the transmission reception delay circuit 232. The orthogonal detecting phase unit 234 generates complex receiving signals by performing orthogonal phase detection of the added and composed receiving signals. The orthogonal detecting phase unit 234 includes a $\pi/2$ phase converter (shifter) 235, mixers 236-1 and 236-2 and low pass filters (LPFs) 237-1 and 237-2.

FIG. 7 further depict a construction of the transmission/reception unit 2 in the diagnosis apparatus main body 10. As explained in FIG. 2, the transmission/reception unit 2 includes a reference signal generator 21, a transmission unit 22 and a reception unit 23. The reference signal generator 21 generates continuous waves or pulse waves having the same frequency to the central frequency of the ultrasound emitted from the transducers 111 in the ultrasound probe 1. The transmission unit 22 provides drive signals to a plurality (M) of transducers 111 arranged in one dimension at the head portion 11 in the ultrasound probe 1. The reception unit 23 adds the receiving signals acquired from the plurality of transducers 111.

The transmission unit 22 includes a rate pulse generator 221, a transmission delaying circuit 222 and a driving circuit 223. The rate pulse generator 221 generates rate pulses for deciding a rate period of transmitting ultrasound by dividing a continuous wave supplied from the reference signal generator 21. The transmission reception delay circuit 222 gives a delaying time for converging transmission ultrasound at a prescribed depth and a delay time for emitting ultrasound in a prescribed direction based on a control signal supplied from the scanning controller 7 (FIG. 2). The transmission reception delay circuit 222 is provided so as to correspond to each of the M-channel transducers 111. The driving circuit 223 generates driving pulses for driving each of the transducers 111 based on the rate pulse having the set delaying time. The driving circuit 223 is also provided for each of the M channels.

Figure 8:
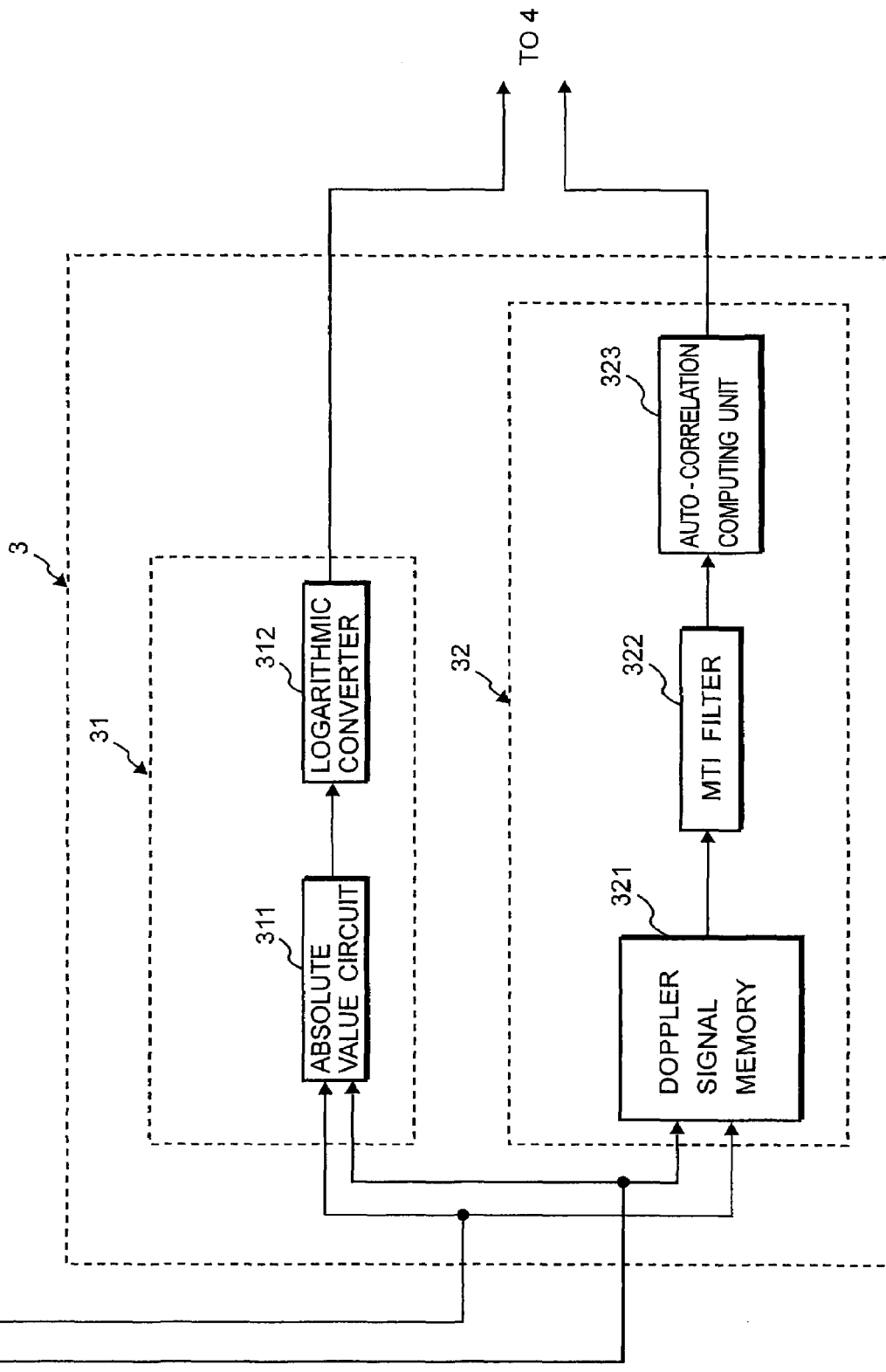
FIG. 8 is a block diagram illustrating a construction of an embodiment of a data generating unit in the ultrasound diagnosis system shown in FIG. 2.

FIG. 8 illustrates a construction of the ultrasound data generator 3 in the diagnosis apparatus of main body 10. The ultrasound data generator 3 includes a B mode data generator 31 for generating B mode data by processing complex receiving signals supplied from the orthogonal detecting phase unit 234 in the reception unit 23, and color Doppler data generator 32 for generating a color Doppler data by processing the complex receiving signals.

The B mode data generator 31 includes an absolute value circuit 311 and a logarithmic converter 312. The absolute value circuit 311 calculates an envelope of receiving signals by executing a absolute value calculation of complex receiving signals supplied from the orthogonal detecting phase unit 234 in the reception unit 23. The logarithmic converter 312 generates B mode data in which a small signal amplitude is relatively emphasized by performing logarithmic conversion of the calculated envelope.

The color Doppler data generator 32 includes a Doppler signal memory 321, an MTI filter 322 and an auto-correlation computing unit 323. The complex receiving signals outputted from the orthogonal detecting phase unit 234 are once stored in a Doppler signal memory 321. The MTI filter 322 is a digital filter for passing a high band pass and removes Doppler components (clatter components) from the complex receiving signals. The clatter components are generated due to fixed reflectors in an organ and breathing movements or pulse movements of the organ. The auto-correlation computing unit 323 calculates self-correlation values for Doppler components of blood flow data extracted through the MTI filter 322. The auto-correlation computing unit 323 further generates color Doppler data by calculating a mean speed, a dispersing value and a power value of the blood flow based on the self-correlation value.

The image data generator 4 includes an image data memory and an image data processing unit (not shown in FIG. 7). Thus, B mode data or color Doppler data acquired and generated at the ultrasound data generator 3 at scanning planes decided by rotation angles $\phi$ of the transducers 111 are stored in the image data memory of the image data generator 4 in correspondence with a plurality of ultrasound transmission/reception directions $\phi1$ to $\phi N$ based on a control of the system controller 9. The B mode data or color Doppler data are processed into two-dimensional image data in the image data processing unit of the image data generator 4. The image data processing unit in the image data generator 4 executes a necessary filtering process to the two-dimensional B mode image data or two-dimensional color Doppler image data generated in the image data memory. The two dimensional image data performed the filtering process is again stored in the image data memory of the image data generator 4.

Display unit 5 includes an angle icon generator 51, a display data generator 52, a data converter 53 and a monitor 54 (FIG. 2). The angle icon generator 51 generates an angle icon in a prescribed format for indicating an angle of the scanning plane based on rotation angle data and rotation drive mode data of the transducers 111 supplied from the rotation angle detecting unit 15 in the ultrasound probe through the rotation mechanism controlling unit 6. For instance, a scanning plane angle $\phi$ in the angle icon indicates $\phi 0$ when a transducers rotation angle before the reversions is zero (0) and a scanning plane angles after the reversion becomes (0+180) degrees when the transducers rotation angle is zero.

The display data generator 52 generates displaying data based the two-dimensional B mode image data and color Doppler image data supplied from the image data generator 4, an angle icon of a scanning plane supplied from the angle icon generator 51 and an object data supplied from the system controller 9. The data converter 53 displays the generated displaying data on a monitor 54 by performing a D/A conversion and a television format. As depicted in FIGS. 11A and 11B, the two-dimensional image data generated in the image data generator 4 is displayed on the display 5 together with an angle icon (Da-2 or Db-2) for indicating an of a scanning plane under a control of the system controller 9.

The rotation mechanism controlling unit 6 in the diagnosis apparatus main body 10 includes a rotation mode change judging unit 61 and a rotation parameter setting unit 62 (FIG. 2) for controlling a rotation drive direction and a driving speed of the head portion 11 in the tip portion 151. The rotation mode change judging unit 61 judges a necessity of exchange from a normal rotation drive mode for acquiring image data to a reverse rotation mode for reversing the head portion 11 at a prescribed angle without acquiring image data based on both the instruction signal supplied from the rotation drive instructing unit 13 in the ultrasound probe 1 and a rotation angle data supplied from the rotation angle detecting unit 15. The rotation parameter setting unit 62 sets rotation drive parameters such as a rotation drive direction and a driving speed of the head portion 11 based on a result of judgment of the rotation mode change judging unit 61. The rotation parameter setting unit 62 further supplies control signals generated based on the rotation drive parameters to the rotating mechanism driver 14 in the ultrasound probe.

A scanning controller 7 in the diagnosis apparatus main body 10 controls directions φ1 to φN of a plurality of ultrasound transmission/reception and orders of the transmission/reception at scanning planes decided by rotation angles of the ultrasound probe head 11 through the transmission unit 22 and the reception unit 23 in the transmission/reception unit 2. An operator inputs an object data, various command signals and also sets image data acquiring conditions through the input unit 8.

The input unit 8 in the diagnosis apparatus main body 10 provides input devices such as a display panel, a key board, a truck ball, a mouse, a selection button and an input button on an operation panel in order to input an object data and various command signals. The input unit 8 further sets an image data acquiring condition and a display condition, a standard driving speed in a normal rotation drive mode and a reverse rotation mode, a CCW reversing angle or a CW reversing angle, and an angle range of a rotation drive of the head portion 11.

The system controller 9 in the diagnosis apparatus main body 10 includes a CPU and a memory circuit for totally controlling operations of each unit the diagnosis system. The various data inputted or set by the input unit 8 are stored in the memory circuit in the system controller 9. Based on the various data, the CPU in the system controller 9 controls each unit in the diagnosis system.

A direction of rotation drive of the head portion 11, a driving speed and a start instruction of rotation drive of the head portion 11 based on direction instruction signal 163 supplied from the rotation instruction unit 13 in the knob handling portion 154 and an angle detection signal 164 supplied from the rotation angle detecting unit 15 are supplied to the rotation mechanism controlling unit 6 in the diagnosis apparatus main body 10. The rotation mechanism controlling unit 6 is performed a control by a control signal supplied from the rotation parameter setting unit 62 in the rotation mechanism controlling unit 6 with judging in the rotation mode change judging unit 61.

The rotation drive control signal outputted from the rotation mechanism controlling unit 6 is supplied to the rotating mechanism driver 14 in the knob handling portion 15 though a signal line 164 in order to generate a driving power for a head rotation. As depicted in FIG. 4, the rotation driving power generated from the rotating mechanism driver 14 is transferred to the rotating mechanism 12 in the tip portion 151 through the angle wire 161. By the driving power supplied the rotating mechanism driver 14, the head portion 11 is driven in a direction and at a speed that are instructed in the rotation drive instructing unit 13. Usually, in this embodiment, the head portion 11 is driven by a step rotation drive. The rotation angle φ of the rotated head portion 11 is always detected by the rotation angle detecting unit 15.

In the embodiment depicted in FIG. 4, a stepping motor is used as the rotating mechanism driver 14 in the knob handling portion 154 since it becomes possible to rotate at a low speed with higher precision. A rotation member of the stepping motor is connected to a support stand of the head rotating mechanism 12 through the angle wire 161. Consequently, the head portion 11 attached free rotatably to the rotating mechanism 12 rotates in the same direction of the rotation direction of the stepping motor at a prescribed speed. Thus, the head portion 11 in the tip portion 151 rotates in a first (counter clockwise: CCW) direction in accordance with a rotation of the stepping motor in the first (CCW) direction.

FIG. 5A illustrates a relationship between a direction of a scanning plane and a rotation drive of the head portion 11 by a driving power supplied from the rotating mechanism driver 14. FIG. 5A illustrates as to how to take up the signal cable 162 in accordance with a rotation drive of the head portion 11. The head portion 11 is constructed with a plurality (M) of transducers 111 arranged in one dimension. In FIG. 5A, an inserting direction of the tip portion 151 into an object indicates a direction of a standard (Y) axis. Thus, the standard direction means when the rotation angle φ of the head portion 11 is a zero (0) degree, i.e., φ=0. A range of the rotation angle φ of the head portion 11 is set so as to rotate from 0 degrees to 180 degrees.

FIG. 5B(a) shows a direction of a scanning plane P when the plurality of transducers 111 is set at the standard direction (φ=0). FIGS. 5B(b) and 5B(c) show a relationship between an arranging direction of the transducers 111 and a direction of a scanning plane P when the head portion 11 rotates in the CCW direction up to a rotation angle φ=90 degrees and φ=180 degrees, respectively. FIGS. 5B(a)-5B(c) further show the storing status of the signal cable 162 connected to each of the transducers 111 when the rotation angle φ of the transducers 111 is 0 degree, 90 degrees and 180 degrees, respectively. As shown in FIG. 5B(a), when the rotation angle φ of the transducers 111 is 0 degree, the cable 162 is stored so as to surround the head portion 11 of a cylinder-shaped peripheral. When the rotation angles φ are respectively 90 degrees and 180 degrees, as shown in FIGS. 5B(b) and 5B(c), the signal cable 162 is respectively stored at a bending status into a vacant space in the tip portion 151. By storing the signal cable 162 in the space portion of the tip portion 151 in accordance with a rotation angle of the head portion 11, it becomes possible to smoothly rotate the transducers 111 connected to the signal cable 162.

FIG. 6 illustrate an outside view of the knob handling portion 154 of the ultrasound probe 1. An angle knob 155 and a rotation drive instructing unit 13 are mounted on knob handling portion 154. The angle knob 155 causes a bending direction and a bending size of the angle portion 152 connected to the tip portion 151. The rotation drive instructing unit 13 instructs as to how to achieve a rotation, such as a method for driving rotation of the transducers 111, a driving speed of the transducers 111 and a driving start of the rotation. The rotation drive instructing unit 13 includes a CW instruction button 131 for inputting an instruction signal for performing a rotation drive in a clockwise direction and a CCW instruction button 132 for performing a rotation drive in a counter clockwise direction. Depending upon how the two buttons 131 and 132 are pushed, it becomes possible to instruct a drive of continuous rotation or a stepping rotation to be selected. Further, it decides a driving speed. Thus, a driving speed can be set in accordance with an amount of pushing power of the push button 131 or 132, or a length of time the push button is pushed. The selection of a continuous rotation drive or a step rotation drive is decided by pushing the button for a prescribed time. For instance, the longer the time the button is pushed the faster driving speed can be set. When the push button is pushed over a prescribed time, a step rotation drive changes to a continuous rotation drive.

Figure 9:
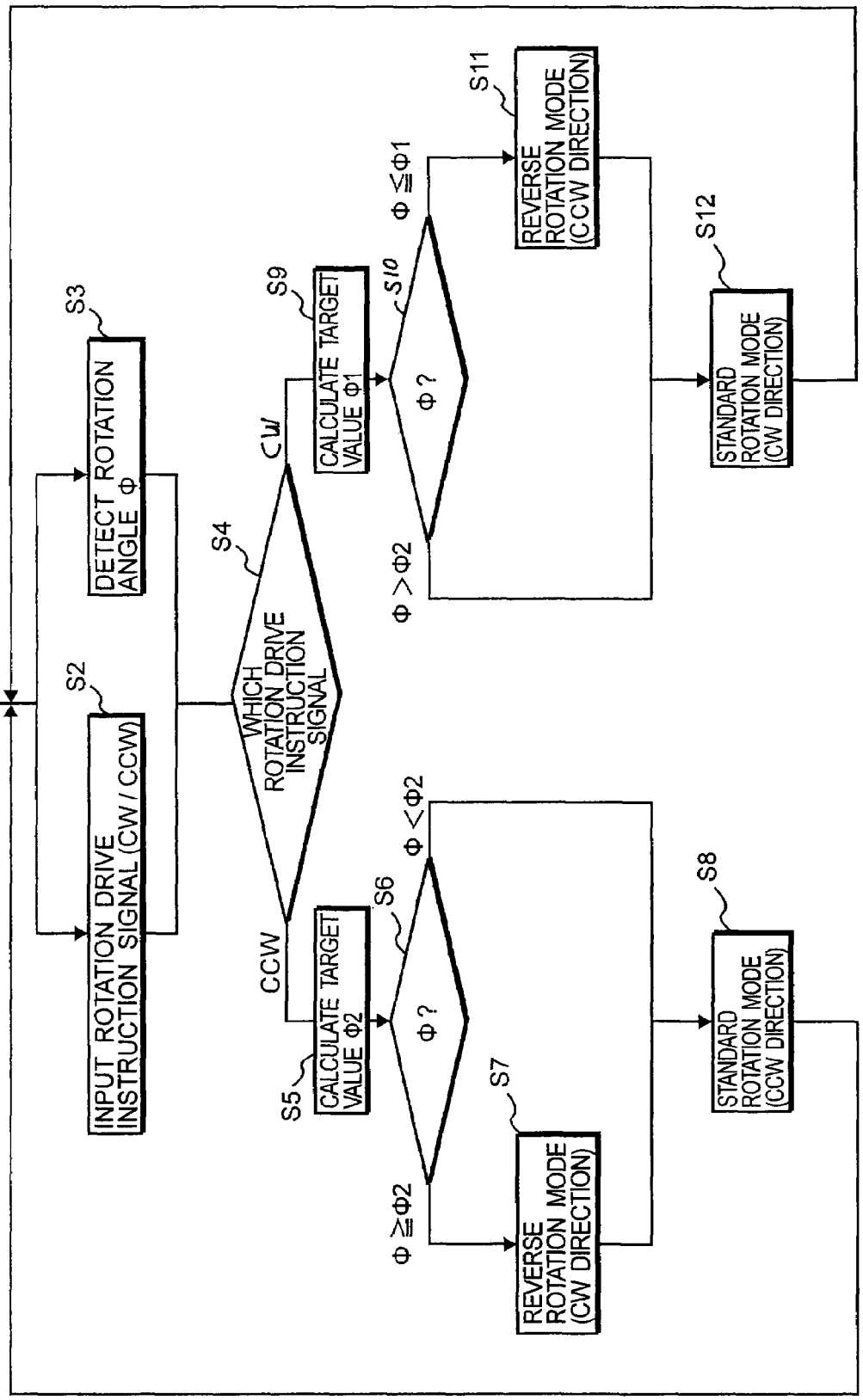
FIG. 9 is a flowchart for explaining control of the rotation drive of the head portion in the motor drive multi-plane type ultrasound probe for the ultrasound diagnosis system, in accordance with the present invention.
Figure 10:
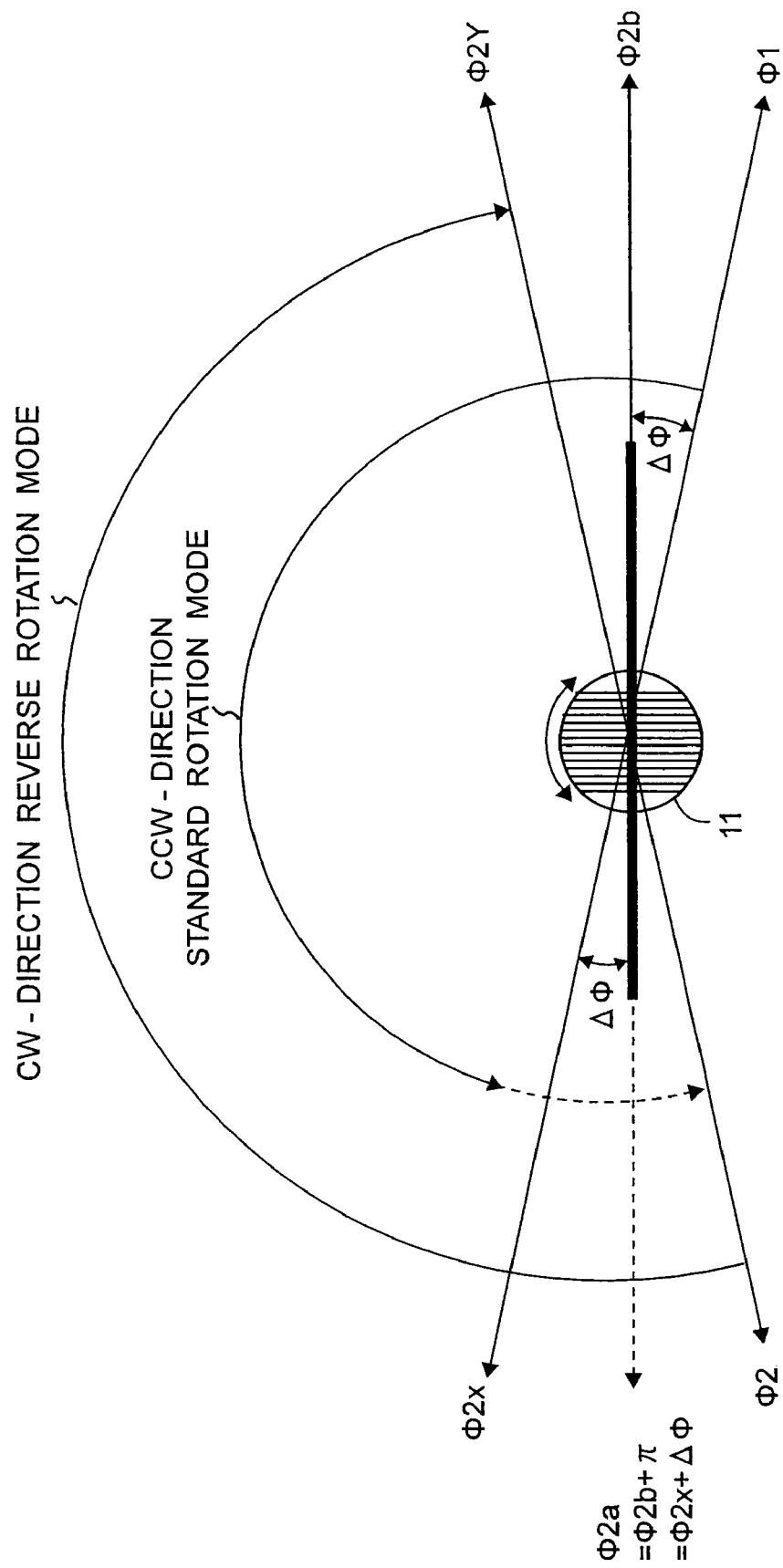
FIG. 10 illustrates rotation drives of the head portion of the motor drive multi-plane ultrasound probe, in accordance with the present invention, in a normal rotation drive mode for acquiring image data in a first direction and a reverse rotation drive mode for reversing transducers in the head portion 180 degrees opposite the first direction.

FIG. 9 is a flowchart of a method for judging a rotation drive mode of the transducers 111 in the rotation mode change judging unit 61 of the rotation mechanism controller 6. FIG. 10 depicts a rotation drive of the head portion 11 in a normal rotation drive mode toward a first (CCW) direction and in a reverse rotation mode toward a second (CW) direction. With reference to FIGS. 9 and 10, a process for judging a rotation drive mode of the transducers 111 in a normal rotation drive mode and a reverse rotation mode, are explained.

As shown in FIG. 10, a range of target angles for a rotation drive is set as angles from $\phi1$ to $\phi2$ where $((\phi2-\phi1)>2\pi)$. In a normal drive condition, the transducers 111 are rotated by a step rotation drive with an angle interval $\Delta\phi$ in a first (CCW) direction up to or exceeding the target angle of 180 degrees. Image data is acquired at a plurality of scanning planes which are decided based on the rotation angle of the transducers 111. Thus, an operator of the ultrasound diagnosis system 10 is initially set so as that the transducers 111 start a rotation drive from the rotation angle $\phi1$ in a normal rotation drive mode toward a first direction for acquiring image data with the step rotation drive by an angle interval $\Delta\phi$. It is also initially set that the normal rotation drive mode is exchanged to a reverse rotation mode when the rotation angle of the transducers 111 reaches a target angle $\phi2$ (hereinafter: "reverse angle $\phi2$"). During the reverse rotation mode, the transducers 111 are reversed to a second direction being 180 degrees opposite to the direction without acquiring image data. Thus, the operator further inputs the target reverse angle $\phi2$ and an adjoin rotation angle $\phi2a$ ($\phi2a=\phi2x-\Delta\phi$) to the reverse angle $\phi2$ under conditions of $\phi2a<\phi2$ and $(\phi2a-\pi)=\phi2b>\phi1$ by using the input unit 8. The operator also sets a driving speed V2 for the reverse rotation mode in the second direction that is faster than a driving speed V1 for the normal rotation drive in the first direction mode, i.e., V2>V1 (FIG. 9, step S1).

After setting the initial conditions, the operator further inputs a CCW rotation drive instructing signal or a CW rotation drive instructing signal as the first direction in the normal rotation drive mode by pushing either one of the push buttons 131 or 132 in the rotation drive instructing unit 13 of the ultrasound probe 1 (FIG. 9, step S2). In this embodiment, it is supposed that a CCW rotation drive instructing signal is inputted. A rotation angle $\phi$ of the transducers 111 in the CCW direction in accordance with the input of the CCW instructing signal is always detected by the rotation angle detecting unit 15 (FIG. 9, step S3).

The rotation mode change judging unit 61 in the rotation mechanism controlling unit 6 judges the instructed direction of a rotation drive for the transducers 111 through the rotation drive instructing unit 13 (FIG. 9, step S4, CCW). The rotation mode change judging unit 61 calculates the target reverse angle $\phi2$ based on a present rotation angle $\phi$ of the transducers 111 (FIG. 9, step S5) and judges a necessity of an exchange of the normal rotation drive mode in the CCW direction to the reverse rotation mode in the CW direction (FIG. 9, step S6). If the transducers 111 have not yet reached to the target reverse angle, e.g., a present rotation angle $\phi$ is smaller than the target reversing angle $\phi2$ (FIG. 9, step S6, $\phi<\phi2$), the rotation mode change judging unit 61 judges to continue the normal rotation drive mode in the CCW direction (FIG. 9, step S8). Based on this judging result, the rotation parameter setting unit 62 generates and supplies a control signal for driving the head portion in the normal rotation mode toward the CCW direction at the driving speed V1 to the rotating mechanism driver 14 in the ultrasound probe 1. The rotating mechanism driver 14 drives the rotating mechanism 12 in accordance with a control signal of the driving speed so as to rotate the transducers 111 in the normal rotation mode toward the CCW direction at the driving speed V1. Thus, image data is acquired at a scanning plane corresponding to the rotation angle $\phi$ of the transducers 111 in the CCW direction, and a two-dimensional image is displayed.

On the other hand, in a situation where the present rotation angle $\phi$ of the transducers 111 detected by the rotation angle detecting unit 15 reached to the target angle $\phi2$ for reversing to an opposite direction ($\phi=\phi2$) and/or exceeded the target angle $\phi2$ ($\phi>\phi2$) (FIG. 9, step S6, $\phi>\phi2$), the rotating mechanism driver 14 drives the rotating mechanism 12 in accordance with a control signal of the driving speed so as to rotate the head portion 11 in the reverse rotation mode toward the CW direction at the driving speed V2. Thus, the rotation mode change judging unit 61 in the rotation mechanism controlling unit 6 makes a determination to change from the normal rotation mode in the CCW direction to the reverse rotation mode in the opposite CW direction rotation by receiving both the angle data $\phi=\phi2$ and the CCW instruction signal. The rotation parameter setting unit 62 in the rotation mechanism controlling unit 6 sets to change to the reverse rotation mode in the CW direction. The rotation parameter setting unit 62 further sets a driving speed V2 and a rotation angle $\phi2Y$ after the reversion. The control signal generated based on these rotation drive parameters is supplied to the rotating mechanism driver 14 of the ultrasound probe 1.

Thus, the rotation parameter setting unit 62 supplies a control signal to the rotating mechanism driver 14 of the ultrasound probe 1 for driving the transducers 111 in the reverse rotation mode toward the CW direction at the driving speed V2. The rotating mechanism driver 14 drives the rotating mechanism 12 in accordance with the control signal. The rotating mechanism driver 14 drives the rotating mechanism 12 based the control signal so as to reverse the transducers 111 in the CW direction at the driving speed V2 until the rotation angle $\phi$ reaches to a reverse angle $\phi2Y$.

Suppose that after reversing the head, the rotation drive instructing unit 13 is still inputting an instruction signal in the normal rotation drive mode in order to acquire image data at a rotation angle ($\phi2Y-\Delta\theta$) adjoined the reversed angle $\phi2Y$ in the CW direction. The rotation drive instructing unit 13 further inputs the CCW instruction signal in order to continue the rotation drive in the normal rotation mode toward the CCW direction when the rotation angle $\phi$ of the transducers 111 reached to the reversed angle $\phi2Y$ in the reverse rotation mode the CW direction so as that image data acquisition is automatically performed.

Image data is acquired at a plurality of scanning planes corresponded with each rotation angle $\phi$ of the transducers 111. For instance, during the normal rotation drive mode in the CCW direction, image data is acquired at each scanning plane of rotation angles $\phi=\phi 2b, \phi 2b+\Delta\phi, \phi 2b+2\Delta\phi, \ldots, \phi 2$. Similarly, during the normal rotation mode in the CCW direction after the reversion of the head portion, image data is acquired at each of scanning planes at the rotation angle $\phi=\phi 2Y, \phi 2Y+\Delta\phi, \ldots, \phi 2x(\phi 2x=2b+\pi-\Delta\phi)$. By exchanging orders of the ultrasound transmission/reception during the normal rotation mode in the CCW direction after the reversion, it becomes possible to replace each of the scanning planes at each of the above mentioned rotation angles $\phi=\phi 2Y, \phi 2b-\Delta\phi, \ldots, \phi 2$ to each of the scanning planes at angles $\phi 2=\phi 2, \phi 2-\Delta\phi=\phi 2Y+\pi-\Delta\phi, \ldots, \phi 2x=\phi 2b+\pi-\Delta\phi)$. Thus, when the rotation drive instructing unit 13 continuously inputs the CCW instruction signal after the reversion, the transducers 111 are again driven in the normal rotation mode after driving in the reverse rotation mode so as to continuously acquire image data in the CCW direction at each scanning plane between the angles $\phi 2Y$ to $\phi 2Y+\pi$.

If the first direction for the normal rotation mode is set as a CW direction, the step S4 in FIG. 9 goes through the steps S9-S12 so that the transducers 111 are driven by a step rotation drive with an interval $\pi\phi$ in an angle range between $\phi 2$ to $\phi 1$ in the CW direction. When the rotation angle $\phi$ of the head portion 11 reaches a prescribed CCW reverse angle, the normal rotation mode in the CW direction is changed to the reverse rotation mode in the CCW direction. Since the following steps S11 and S12 are substantially similar to the above-explained steps S7 and S8, the same explanation need not be repeated.

To acquire image data through the transducers in a normal rotation drive mode before and after the reversion, the scanning controller controls so that an order of acquisition of image data after the reversion reverses to an order of acquisition of image data before the reversion, in order to keep the scanning order of the ultrasounds. Thus, the scanning controller 7 in FIG. 2 sets directions of ultrasound transmission/reception at scanning planes by controlling delay times of the transmission delaying circuit 222 in the transmission unit 22 and the reception delaying circuit 232 in the reception unit 23. In this situation, it becomes possible to consider that each of scanning planes at angles $\phi 2Y, \phi 2Y+\Delta\phi, \ldots, \phi 2$ x after the reversion in the normal rotation drive mode as the scanning planes at angles $\phi=\phi 2Y+\pi, \phi 2Y+\pi-\Delta\phi, \ldots, \phi 2Y+\pi+(\pi-\Delta\phi)$ by exchanging the orders of ultrasound transmission/reception.

As depicted in FIG. 10, it is possible to prevent reversions from frequently occurring when a further rotation drive of the head portion in the CCW direction just after the reversion in the CW direction by setting that the rotation angle $\phi 2a$ just after the reversion as $\phi 2a>\phi 2$, and the CW reversion angle $\phi 2y$ as $\phi 2a>\phi 2y>\phi 1$ in the target angle range between $\phi 1$ and $\phi 2$ of the rotation drive. Consequently, it becomes possible to prevent a deterioration of continuity of image data before and after the reversion from appearing by acquiring image data at a scanning plane $\phi=\phi 2y+\Delta\phi$ adjoining to the scanning plane $\phi=\phi 2$. Further, it can avoid increasing a load to the rotating mechanism and the rotating mechanism driver.

FIGS. 11A and 11B depict examples of display data displayed on a monitor 54 in the display unit 5. FIG. 11A shows an image data Da-1 and an angle icon Da-2 indicating a scanning plane angle $\phi 2$ by a direction marker Dm. The image data Da-1 is acquired through the head portion at a rotation angle $\phi 2$ just before the reversion by an ultrasound transmission/reception order of $\theta 1, \theta 2, \ldots, \theta N$. FIG. 11B shows an image data Db-1 acquired by a scanning plane at the angle $\phi 2y$ just after the reversion and an angle icon Db-2 of the scanning plane. By exchanging the scanning order of the ultrasound transmission/reception just after the reversion at a reversed angle $\phi 2y$ as the opposite order of $\theta N, \theta N-1, \theta-2, \ldots, \phi 1$, it can acquire image data successive to the image data acquired by a scanning plane at the reversion target angle $\phi 2$.

The image data Da-1 and Db-1 are originally displayed so as to replace an order from a right side with an order from a left side since the rotation angle $\phi 1x$ of the transducers at just after the reversion differs almost 180 degrees from the rotation angle $\phi 2b$ of the transducers at just before the reversion. However, as explained the above, it becomes possible to acquire the image data Db-1 at a scanning plane $\phi 2y$ just after the reversion by proceeding to the image data Da-1 acquired at the scanning plane angle $\phi 2$ just before the reversion, because the image data acquired at just after the reversion is generated by exchanging transmission/reception orders of the ultrasound probe.

The scanning plane direction marker Dm displayed in the angle icon Da-2 or Db-2 moves in the CCW direction before and after the reversion in accordance with a rotation drive of the head portion in the CCW direction. It is further possible to accurately set an angle of the head portion by adding each angle values $\phi 2$, or $\phi 2y$ of the scanning plane direction marker Dm in the angle icon Da-2 or Db-2.

According to an embodiment consistent with the present invention, it becomes possible to easily acquire image data at the scanning planes over the reversion angle to the same scanning planes before the reversion by automatically reversing the plurality of transducers arranged in the head portion by 180 degrees when the plurality of transducers is rotated to or over the reversion angle.

This means that, although a rotation drive of the transducers are limited in the prescribed angle range, it can acquire image data at the scanning planes by exceeding the prescribed angle range when the rotation drive instructing signal is successively input. Thus, it becomes possible to successively input an instruction signal for rotating the head portion in a desired rotation drive direction without taking care of an arrival time of the transducers to the reversion angle. Accordingly, it can easily acquire the successive scanning planes in a desired rotation drive direction in a short time. This improves efficiency of the inspection and reduces burdensome operations of an operator.

The present invention can improve a continuity of displaying image data acquired just before the reversion of the head portion and image data acquired just after the reversion by setting such that a driving speed for a reverse rotation mode is faster than a driving speed for a normal rotation drive mode. Further, the present invention can observe image data acquired after the reversion by proceeding to image data acquired before the reversion by exchanging scanning orders of the ultrasound transmission and/or reception. Of course, it is also possible to keep a continuity of images by displaying image data that is acquired just before the reversion as a stationary image until image data acquired just after the reversion can be displayed in order to continuously display image data acquired at a plurality scanning planes both before the reversion and after the reversion.

According to the present invention, it becomes possible to construct the head portion of the probe in a compact size with a high reliability because the plurality of transducers arranged in the head portion are directly connected to each signal line. According to the present invention, it further becomes possible to acquire image data of a good quality without using the slip ring which causes slipping noises to occur.

In the above-explained embodiment, the transducers drive a step rotation with a $\Delta\phi$ interval in the normal rotation drive mode. Of course, it is possible to drive the transducers in the normal rotation drive mode by a continuous rotation. When the transducers are driven in the CCW direction with the step rotation, the transducers are shifted by an angle Δφ with each pushing of the CCW instruction button 132 in the rotation drive instructing unit 13. If the CCW instruction button 132 is further pushed when the transducers reach the reversion angle φ2, the transducers rotate in the reverse rotation mode. On the contrary, if the transducers are driven in the CCW direction by the continuous rotation, once the CCW instruction button 132 of the rotation drive instructing unit 13 is pushed, the transducers are continuously driven up to the reversion angle φ2 with the continuous rotation drive and automatically change to the reverse rotation mode when the rotation angle reaches the reversion angle φ2.

In FIG. 12, the rotation drive instruction unit 13 in the knob handling portion 154 further includes a mode changing switch 133 for inputting manually a change to the reverse rotation mode. If an operator does not want to automatically drive the transducers in the reverse rotation mode, the transducers are once stopped at the reversion angle. Then, the operator inputs an instruction signal for driving the transducers in the reverse rotation mode by operating mode changing switch 133.

In the above-explained embodiment, data is acquired in the normal rotation drive mode after the reversion is performed by exchanging the scanning orders of ultrasound transmission/reception. It is, of course, possible to acquire image data using the same scanning order of ultrasound transmission/reception both before and after the reversion in the normal rotation drive mode. In this case, the image data acquired after the reversion in the normal rotation drive mode a scanning order from the right side is replaced with a scanning order from the left side in order to continuously display the image data on the monitor.

Figure 13:
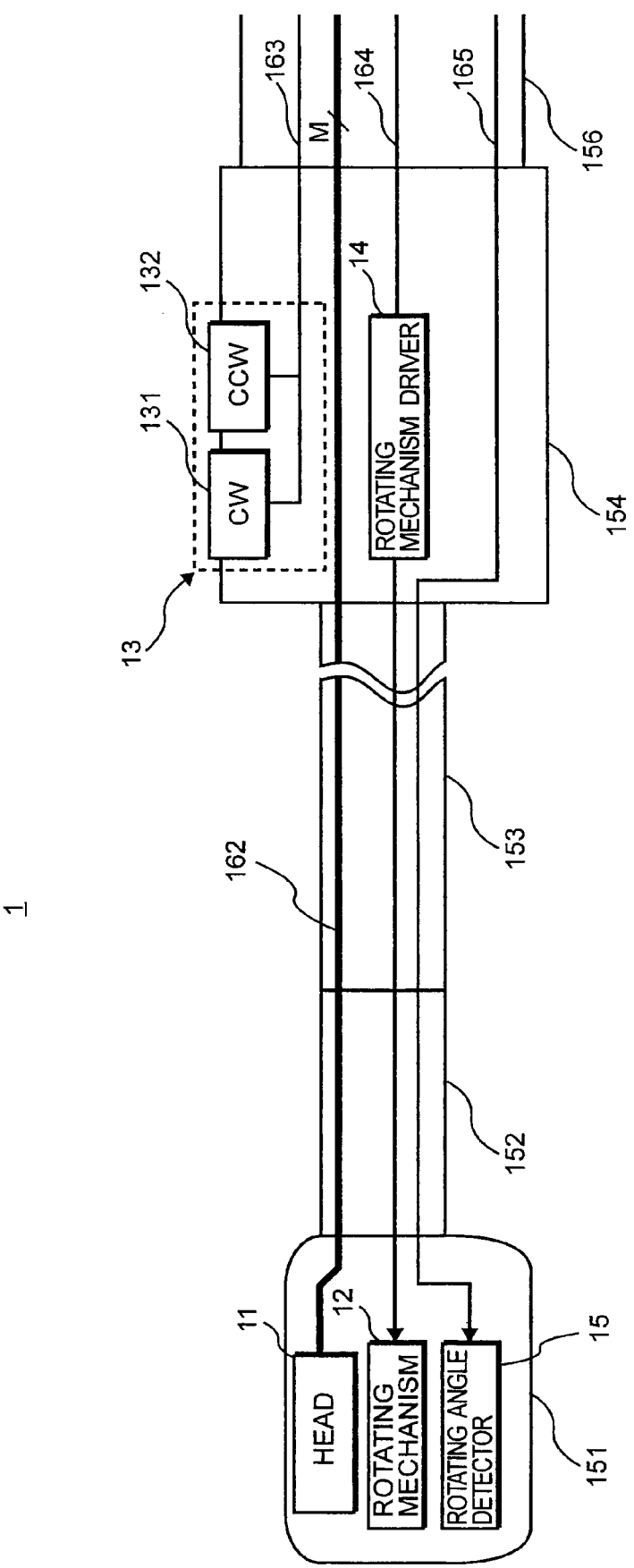
FIG. 13 illustrates another embodiment of the head portion of the ultrasound probe.

FIG. 13 depicts another embodiment of the ultrasound probe 1 in which the rotation angle detecting unit 15 is provided in the tip portion 151 of the ultrasound probe 1 in order to make the tip portion in a small size. To do so, the rotation angle detecting unit 15 is constructed, for instance, by using an MR element. Although the construction of the tip portion 151 becomes complicated, it becomes possible to directly detect an accurate rotation angle of the head portion.

In the rotation drive instructing unit of the above-explained embodiment, the rotation drive instruction buttons are provided in the knob handling portion of the ultrasound probe. Of course, it is also possible to input the rotation drive instruction through a display panel or an input device.

In the above-explained embodiment, the data acquisition performs successive processes as that the normal rotation drive mode before the reversion; i.e., the reverse rotation mode to the normal rotation drive mode after the reversion. It is also possible to directly go to the normal rotation drive mode after the reversion from the normal rotation drive mode before the reversion by setting a desired scanning plane of the transducers in the normal rotation drive mode after the reversion. This can improve the efficiency of an inspection.

Although the acquisition of image data is not performed during a reverse rotation mode in the above-mentioned embodiment, it is possible to prohibit displaying image data acquired during a reverse rotation mode. As explained above, it is possible to improve a continuity of display of image data acquired in the normal rotation drive mode by displaying the image data acquired in a normal rotation drive mode just before the reversion as a static image until when the image data acquired in a normal rotation drive mode just after the reversion is displayed.

The above-mentioned embodiment explains a trans-esophageal probe applicable to ultrasound diagnosis. Of course, the present invention is not limited to this ultrasound probe used for a trans-esophageal ultrasound diagnosis. For example, the present invention is applicable to another probe for insertion into body cavities, such as an endo-vaginal probe for using diagnosis of a fetus, a uterus or an ovary, and an endo-bowel probe for examination of a prostate. In a trans-esophageal probe, a tip portion for inserting into a head portion is coupled to a knob handling portion through a flexible trans-guiding portion. On the contrary, an endo-vaginal probe or an endo-bowel probe is comprised of a rigid insertion portion.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

The invention claimed is:

1. An ultrasound diagnosis system including a motor driving a multi-plane ultrasound probe for acquiring image data at a voluntary scanning plane by rotating a plurality of transducers arranged in a head portion in a prescribed target angle range, the ultrasound diagnosis system comprising:
   a rotation drive instructing unit configured to cause rotation drive of the head portion;
   a rotation angle detecting unit configured to detect a rotation angle of the head portion;
   a rotation mechanism driving unit configured to drive rotation of the head portion; and
   a rotation mechanism controlling unit configured to control the rotation mechanism driving unit based on both a rotation drive instruction signal supplied from the rotation drive instructing unit and a rotation angle detection signal supplied from the rotation angle detecting unit,
   wherein the rotation mechanism controlling unit is configured to control a rotation drive of the plurality of transducers in a normal rotation drive mode for acquiring image data in the prescribed target angle range in a first direction, and to control the rotation drive of the plurality of transducers in a reverse rotation drive mode in a second direction opposite to the first direction up to a prescribed reversing angle automatically in response to the rotation of the head portion exceeding the target angle range; and
   the rotation mechanism controlling unit is further configured to control a rotation drive of the head portion under the normal rotation drive mode in the first direction when the rotation drive instruction signal is further supplied.

2. The ultrasound diagnosis system according to claim 1, wherein the rotation mechanism controlling unit includes:
   a rotation drive mode change judging unit configured to change from the normal rotation drive mode to the reverse rotation drive mode based on both the rotation drive instruction signal and the rotation angle detection signal; and
   a rotation drive parameter setting unit configured to set rotation drive parameters including a rotation drive speed of the head portion and a target angle for the rotation drive in the normal rotation drive mode or the reverse rotation drive mode based on a judging result of the rotation drive mode change judging unit and to control the rotation mechanism driving unit based on control signals of the set rotation drive parameters.

3. The ultrasound diagnosis system according to claim 2, wherein:
the rotation drive parameter setting unit is configured to set a normal rotation drive speed for driving rotation of the transducers in the target angle range toward the first direction under the normal rotation drive mode, and to set a reversing speed for reversing the head portion toward the second direction in a reverse rotation drive mode, the reversing speed being greater than the normal rotation drive speed.

4. The ultrasound diagnosis system according to claim 1, wherein:
the rotation mechanism controlling unit is configured to reverse the direction of the transducers toward the second direction equal to or more than an angle of 180 degrees when the rotation angle detecting unit detects that the transducers have driven in the first direction equal to or exceeding the target angle range.

5. The ultrasound diagnosis system according to claim 1, wherein:
the rotation drive instructing unit includes a CW instruction button for causing the transducers to rotate in a clockwise direction and a CCW instruction button for instructing the transducers to rotate in a counter clockwise direction; and
a rotation drive speed of the transducers and a selection of a continuous rotation drive of the transducers or a step rotation drive of the transducers is set by a pushing strength or a pushing time of either one of the buttons.

6. The ultrasound diagnosis system according to claim 1, wherein:
the rotation drive instructing unit further includes a rotation drive mode change instructing switch for ceasing the rotation drive of the transducers in the first direction when the rotation drive of the transducers in the first direction reaches a reversing target angle; and
the rotation mechanism controlling unit is configured to reverse the transducers to rotate in the second direction based on a rotation drive mode change instructing signal supplied from the rotation drive mode change instructing switch.

7. The ultrasound diagnosis system according to claim 1, further comprising:
a scanning control unit configured to control directions and orders of transmission and reception of the transducers at scanning planes based on a rotation angle of the transducers; and
the scanning control unit is configured to reverse a scanning order of the ultrasound transmission and reception for acquiring image data after the reversion so as to keep the same scanning order of the ultrasound transmission and reception for obtaining image data before the reversion, when the transducers acquire image data under the normal rotation drive mode before and after the reversion.

8. The ultrasound diagnosis system according to claim 1, further comprising:
a display unit configured to display images being generated based on image data acquired through the transducers, wherein the display unit is configured to display image data acquired after the reversion by exchanging a scanning order from a right side for the image data acquired before the reversion with a scanning order from the left side in order to successively display image data acquired at a plurality of scanning planes of the transducers in the normal rotation drive mode both before the reversion and after the reversion.

9. The ultrasound diagnosis system according to claim 8, wherein:
the display unit is configured to display image data acquired just before the reversion as a stationary image until a display of image data acquired just after the reversion is started in order to successively display image data acquired at a plurality of scanning planes of the transducers in the normal rotation drive mode both before and after the reversion.

10. The ultrasound diagnosis system according to claim 8, wherein:
the display unit is configured to display image data acquired under the normal rotation drive mode before and after the reversion together with angle icons for indicating each rotation angle of the scanning plane of the transducers in the normal rotation drive mode.

11. The ultrasound diagnosis system according to claim 1, wherein:
the motor drive multi-plane type ultrasound probe includes a tip portion for inserting into a body of an object and an angle portion connected to the tip portion; and
the ultrasound probe is coupled to a main body of the ultrasound diagnosis system by connecting the angle portion to the rotation drive instructing unit in the main body through an angle knob-handling portion and a trans-guiding portion of the probe.

12. A scanning method for an ultrasound diagnosis system including a motor driving a multi-plane type ultrasound probe for acquiring image data at voluntary rotation angles by rotating a plurality of transducers arranged in a head portion toward a target rotation angle, the scanning method comprising:
setting rotation drive parameters of the plurality of transducers;
inputting a rotation drive instruction signal for the plurality of transducers;
detecting a detection signal of a present rotation angle of the plurality of transducers; and
controlling a drive of a rotation drive mechanism of the plurality of transducers based on both the rotation drive instruction signal for the head portion and the detection signal of the rotation angle,
wherein the controlling step includes controlling a rotation drive of the plurality of transducers under a normal rotation drive mode for acquiring image data in a target range of rotation angle in a first direction and controlling the rotation drive of the plurality of transducers under a reverse rotation drive mode in a second direction opposite to the first direction by a prescribed angle automatically in response to the rotation of the plurality of transducers exceeding the target rotation angle in the first direction; and
the controlling step further includes controlling the rotation drive of the transducers under the normal rotation drive mode in the first direction when the rotation drive instruction signal is further supplied.

13. The scanning method according to claim 12, wherein the controlling step further comprises:
judging a mode change from the normal rotation drive mode to the reverse rotation drive mode based on the rotation drive instruction signal and the rotation angle detection signal;
setting rotation drive parameters including a rotation drive speed of the plurality of transducers and the target rotation angle for the rotation drive of the plurality of transducers in the normal rotation drive mode or the reverse rotation drive mode based on a result of the judgment; and controlling the driving of the rotation drive mechanism based on control signals decided by the set rotation drive parameters.

14. The scanning method according to claim 13, wherein;

the setting of the rotation drive parameters as a reversing speed for reversing the plurality of transducers in the second direction in the reverse rotation drive mode is faster than a normal rotation drive speed for driving the plurality of transducers in the first direction during the normal rotation drive mode.

15. The data acquiring method for the ultrasound diagnosis system according to claim 12, further comprising:

pushing either a CW instruction button so as to rotate the plurality of transducers in a clockwise direction or a CCW instruction button so as to rotate the plurality of transducers in a counter-clockwise direction;

setting a rotation drive speed of the plurality of transducers by a pushing strength of either one of the instruction buttons; and selecting a continuous rotation drive or a step rotation drive of the plurality of transducers by a pushing time length of either one of the instruction buttons.

* * * * *